US007479270B2

(12) United States Patent
McColl et al.

(10) Patent No.: US 7,479,270 B2
(45) Date of Patent: Jan. 20, 2009

(54) METHODS AND COMPOSITIONS FOR ACTIVATING VEGF-D AND VEGF-C

(75) Inventors: Bradley McColl, Victoria (AU); Megan E. Baldwin, Victoria (AU); Steven Stacker, Victoria (AU); Marc Achen, Victoria (AU)

(73) Assignee: Vegenics Limited, Toorak, Victoria (AU)

( * ) Notice: Subject to any disclaimer, the term of this patent is extended or adjusted under 35 U.S.C. 154(b) by 6 days.

(21) Appl. No.: 10/522,232

(22) PCT Filed: Jul. 21, 2003

(86) PCT No.: PCT/US03/22521

§ 371 (c)(1),
(2), (4) Date: Jul. 8, 2005

(87) PCT Pub. No.: WO2004/009773

PCT Pub. Date: Jan. 29, 2004

(65) Prior Publication Data

US 2005/0282228 A1 Dec. 22, 2005

Related U.S. Application Data

(60) Provisional application No. 60/485,741, filed on Jul. 10, 2003, provisional application No. 60/445,234, filed on Feb. 6, 2003, provisional application No. 60/397,580, filed on Jul. 23, 2002.

(51) Int. Cl.
*A61K 38/43* (2006.01)
*A61K 38/48* (2006.01)
*C07K 14/435* (2006.01)

(52) U.S. Cl. .................. 424/94.64; 424/94.1
(58) Field of Classification Search ........................ None
See application file for complete search history.

(56) References Cited

U.S. PATENT DOCUMENTS

| 4,645,668 | A |   | 2/1987 | Pinnell |
| 5,304,118 | A |   | 4/1994 | Trese et al. |
| 5,520,912 | A | * | 5/1996 | Eibl et al. ................. 424/94.64 |

FOREIGN PATENT DOCUMENTS

| DE | 10141749 | 3/2002 |
| GB | 985498 | 3/1965 |
| WO | WO 91/11193 | 8/1991 |
| WO | WO-91/11193 | 8/1991 |
| WO | WO 95/24473 | 9/1995 |
| WO | WO 96/11269 | 4/1996 |
| WO | WO 96/26736 | 9/1996 |
| WO | WO 98/07832 | 2/1998 |
| WO | WO 99/08522 | 2/1999 |
| WO | WO-00/18436 | 4/2000 |
| WO | WO 00/18436 | 4/2000 |
| WO | WO 00/37025 | 6/2000 |
| WO | WO 01/62799 | 8/2001 |
| WO | W O 02/17958 | 3/2002 |
| WO | WO 02/057299 | 7/2002 |

OTHER PUBLICATIONS

Olofsson et al., Proc. Natl. Acad. Sci. USA, Sep. 1998, vol. 95, pp. 11709-11714, especially abstract and p. 11712, col. 1, paragraph 2.
Plouet et al., J. Biol. Chem., May 1997, vol. 272, No. 20, pp. 13390-13396, especially abstract and p. 13393.
Stacker et al., J. Biol. Chem., Nov. 1999, vol. 274, No. 45, pp. 32127-32136, especially abstract, p. 32127, col. 2 to p. 32128, paragraph 1, and p. 32130.
Enholm et al., Trends in Cardiovascular Medicine, 1998, vol. 8, No. 7, pp. 292-297, especially Figure 2 at p. 294.
Bell, William R., M.D.; "The Fibrinolytic System in Neoplasia," *Seminars in Thrombosis and Hemostasis*, vol. 22 (6), pp. 459-478 (1996).
Carmeliet, Peter, et al.; "Insights in Vessel Development and Vascular Disorders Using Targeted Inactivation and Transfer of Vascular Endothelial Growth Factor, the Tissue Factor Receptor, and the Plasminogen System," *Annals New York Acacemy of Sciences*, pp. 191-206, XP009083100.
European Search Report for European Application No. 03765736.8; mailed May 15, 2007.
Wang, et al., "Induction of KDR Expression in Bovine Arterial Endothelial Cells by Thrombin: Involvement of Nitric Oxide," *Journal of Cellular Physiology*, vol. 190, pp. 238-250 (2002).
European Search Report, EP 03765736, European Patent Office, mailed Nov. 2, 2007.
Ueda et al., Correlation between vascular endothelial growth factor-C expression and invasion phenotype in cervical carcinomas, Int. J. Cancer Res., 98:335-343, 2002.
Achen et al., Localization of vascular endothelial growth factor-D in malignant melanoma suggests a role in tumour angiogenesis, J. Pathol., 193:147-154, 2001.
Achen et al., Monoclonal antibodies to vascular endothelial growth factor-D block its interactions with both VEGF receptor-2 and VEGF receptor-3, Eur. J. Biochem., 267:2505-2515, 2000.
Achen et al., Vascular endothelial growth factor D (VEGF-D) is a ligand for the tyrosine kinases VEGF receptor 2 (Flk1) and VEGF receptor 3 (Flt4), PNAS USA, 95:548-553, 1998.
Andreasen et al., The plasminogen activation system in tumor growth, invasion, and metastasis, Cell. Mol. Life Sci., 57:25-40, 2000.

(Continued)

*Primary Examiner*—Christine J Saoud
(74) *Attorney, Agent, or Firm*—Marshall, Gerstein & Borun LLP

(57) ABSTRACT

Methods for activating endothelial growth factors VEGF-C or VEGF-D with plasmin, and methods of treatment comprising administering a phamarceutical compositions comprising plasmin. Also disclosed are methods for screening for inhibitors of activation of the growth factors by plasmin, and method of treatment by blocking activation of VEGF-C/D activation by plasmin. Further disclosed are methods for screening for other proteases that activate VEGF-C/D, and for inhibitors of such activation. The invention further includes inhibitors of plasmin activity and methods of treating patients in need thereof with said inhibitors.

11 Claims, 4 Drawing Sheets

OTHER PUBLICATIONS

Baldwin et al., Multiple forms of mouse vascular endothelial growth factor-D are generated by RNA splicing and proteolysis, J. Biol. Chem., 276:44307-44314, 2001.

Bell, The fibrinolytic system in neoplasia, Seminars in Thrombosis and Hemostasis, 22:459-478, 1996.

Brown et al., Biotinylated and cysteine-modified peptides as useful reagents for studying the inhibition of cathepsin G, Anal. Biochem., 217:139-147, 1994.

Bugge et al., Growth and dissemination of Lewis lung carcinoma in plasminogen-deficient mice, Blood, 90:4522-4531, 1997.

Byzova et al., Adenovirus encoding vascular endothelial growth factor-D induces tissue-specific vascular patterns in vivo, Blood, 99:4434-4442, 2002.

Cao et al., Vascular endothelial growth factor C induces angiogenesis in vivo, PNAS USA, 95:14389-14394, 1998.

Carmeliet et al., Insights in vessel development and vascular disorders using targeted inactivation and transfer of vascular endothelial growth factor, the tissue factor receptor, and the plasminogen system, Ann. N.Y. Acad. Sci., 811:191-206, 1997.

Collen et al., Basic and clinical aspects of fibrinolysis and thrombolysis, Blood, 78:3114-3124, 1991.

Connolly, Vascular permeability factor: a unique regulator of blood vessel function, J. Cell. Biochem., 47:219-223, 1991.

Enholm et al., Vascular endothelial growth factor-C: a growth factor for lymphatic and blood vascular endothelial cells, Trends Cardiovasc. Med., 8:292-297, 1998.

Ferrara et al., The vascular endothelial growth factor family of polypeptides, J. Cell. Biochem., 47:211-218, 1991.

Folkman et al., Angiogenesis, J. Biol. Chem., 267:10931-10934, 1992.

He et al., Suppression of tumor lymphangiogenesis and lymph node metastasis by blocking vascular endothelial growth factor receptor 3 signaling, J. Natl. Cancer Inst., 94:819-825, 2002.

Houck et al., Dual regulation of vascular endothelial growth factor bioavailability by genetic and proteolytic mechanisms, J. Biol. Chem., 267:26031-26037, 1992.

Joukov et al., A novel vascular endothelial growth factor, VEGF-C, is a ligand for the Flt4 (VEGFR-3) and KDR (VEGFR-2) receptor tyrosine kinases, EMBO J., 15:290-298, 1996.

Joukov et al., Proteolytic processing regulates receptor specificity and activity of VEGF-C, EMBO J., 16:3898-3911, 1997.

Kaipainen et al., Enhanced expression of the tie receptor tyrosine kinase messenger RNA in the vascular endothelium of metastatic melanomas, Cancer Res., 54:6571-6577, 1994.

Kaipainen et al., Expression of the fms-like tyrosine kinase 4 gene becomes restricted to lymphatic endothelium during development, PNAS USA, 92:3566-3570, 1995.

Mandriota et al., Vascular endothelial growth factor-C-mediated lymphangiogenesis promotes tumour metastasis, EMBO J., 20:672-682, 2001.

Marconcini et al., c-fos-induced growth factor/vascular endothelial growth factor D induces angiogenesis in vivo and in vitro, PNAS USA, 96:9671-9676, 1999.

Mueller et al., Overexpression of plasminogen activator inhibitor 2 in human melanoma cells inhibits spontaneous metastasis in scid/scid mice, PNAS USA, 92:205-209, 1995.

Nakamura et al., Prognostic significance of vascular endothelial growth factor D in breast carcinoma with long-term follow-up, Clin. Cancer Res., 9:716-721, 2003.

Olofsson et al., Vascular endothelial growth factor B (VEGF-B) binds to VEGF receptor-1 and regulates plasminogen activator activity in endothelial cells, PNAS USA, 95:11709-11714, 1998.

Olofsson et al., Vascular endothelial growth factor B, a novel growth factor for endothelial cells, PNAS USA, 93:2576-2581, 1996.

Paavonen et al., Vascular endothelial growth factor receptor-3 in lymphangiogenesis in wound healing, Am. J. Pathol., 156:1499-1504, 2000.

Partanen et al., VEGF-C and VEGF-D expression in neuroendocrine cells and their receptor, VEGFR-3, in fenestrated blood vessels in human tissues, FASEB J., 14:2087-2096, 2000.

Plouët et al., Extracellular cleavage of the vascular endothelial growth factor 189-amino acid form by urokinase is required for its mitogenic effect, J. Biol. Chem., 272:13390-13396, 1997.

Skobe et al., Induction of tumor lymphangiogenesis by VEGF-C promotes breast cancer metastasis, Nat. Med., 7:192-198, 2001.

Stacker et al., A mutant form of vascular endothelial growth factor (VEGF) that lacks VEGF receptor-2 activation retains the ability to induce vascular permeability, J. Biol. Chem., 274:34884-34892, 1999.

Stacker et al., Biosynthesis of vascular endothelial growth factor-D involves proteolytic processing which generates non-covalent homodimers, J. Biol. Chem., 274:32127-32136, 1999.

Stacker et al., The role of tumor lymphangiogenesis in metastatic spread, FASEB J., 16:922-934, 2002.

Stacker et al., VEGF-D promotes the metastatic spread of tumor cells via the lymphatics, Nat. Med., 7:186-191, 2001.

Szuba et al., Therapeutic lymphangiogenesis with human recombinant VEGF-C, FASEB J., 16:1985-1987, 2002.

Veikkola et al., Signalling via vascular endothelial growth factor receptor-3 is sufficient for lymphangiogenesis in transgenic mice, EMBO J., 20:1223-1231, 2001.

Wang et al., Induction of KDR expression in bovine arterial endothelial cells by thrombin: involvement of nitric oxide, J. Cell. Physiol., 190:238-250, 2002.

White et al., Vascular endothelial growth factor-D expression is an independent prognostic marker for survival in colorectal carcinoma, Cancer Res., 62:1669-1675, 2002.

Wise et al., Vascular endothelial growth factor (VEGF)-like protein from orf virus NZ2 binds to VEGFR2 and neuropilin-1, PNAS USA, 96:3071-3076, 1999.

Yao et al., Age and growth factors in porcine full-thickness wound healing, Wound Repair Regen., 9:371-377, 2001.

Yokoyama et al., Vascular endothelial growth factor-D is an independent prognostic factor in epithelial ovarian carcinoma, Br. J. Cancer, 88:237-244, 2003.

\* cited by examiner

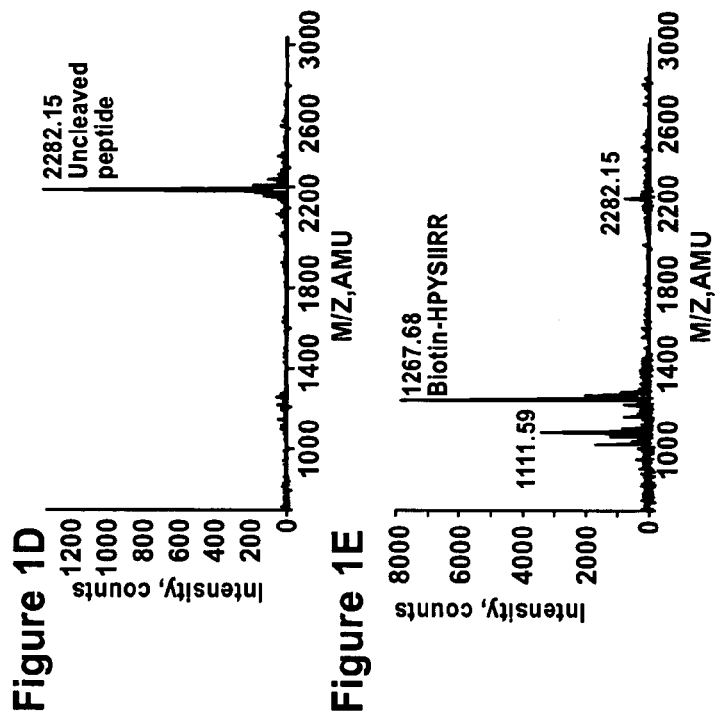
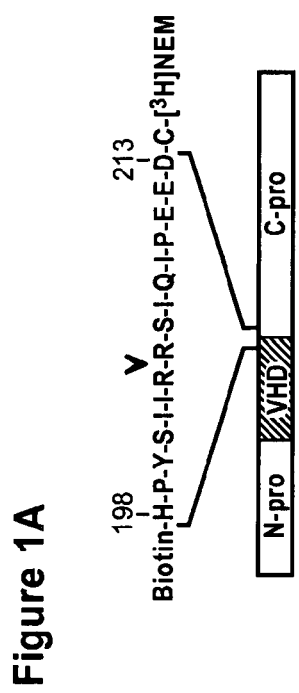
Figure 1A
Figure 1B
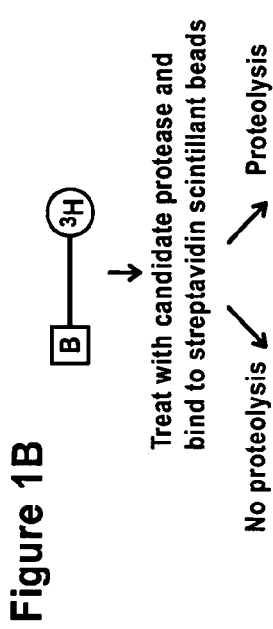
Figure 1C
Figure 1D
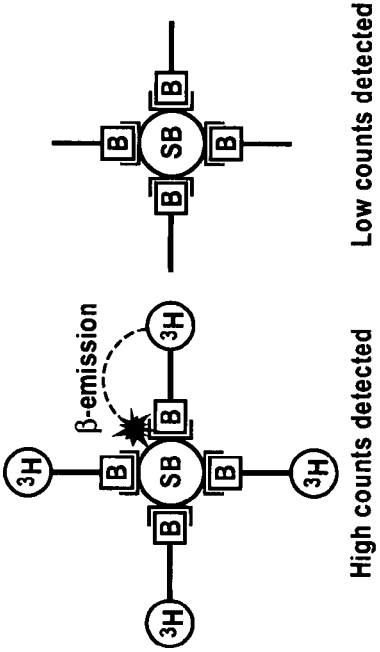
Figure 1E

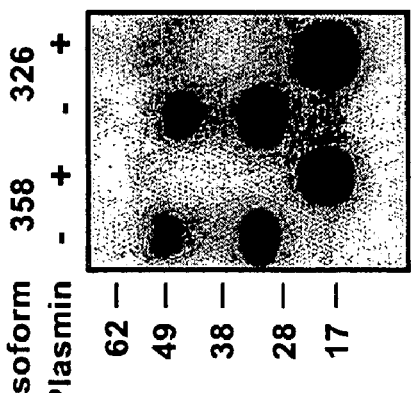
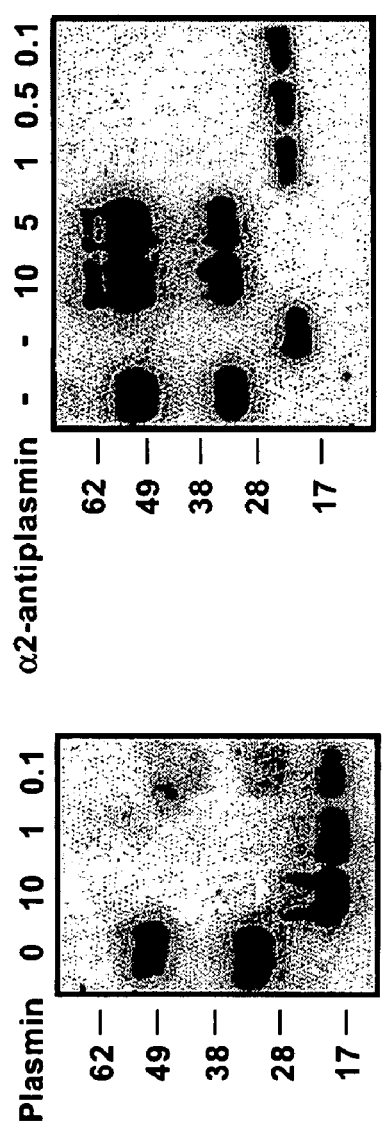

METHODS AND COMPOSITIONS FOR ACTIVATING VEGF-D AND VEGF-C

FIELD OF THE INVENTION

This invention relates to methods for activating endothelial growth factors, and in particular to methods for activating vascular endothelial growth factor D and vascular endothelial growth factor C with plasmin. The invention also relates to methods and assays for identifying activation and/or inhibition factors for said endothelial growth factors, including VEGF-D and VEGF-C.

BACKGROUND OF THE INVENTION

Angiogenesis is a fundamental process required for normal growth and development of tissues, and involves the proliferation of new capillaries from pre-existing blood vessels. Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis, and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor α (TGFα), and hepatocyte growth factor (HGF). See, for example, Folkman et al., "Angiogenesis", *J. Biol. Chem.*, 267: 10931-10934, 1992, for a review.

It has been suggested that a particular family of endothelial cell-specific growth factors and their corresponding receptors is primarily responsible for stimulation of endothelial cell growth and differentiation, and for certain functions of the differentiated cells. These factors are members of the PDGF family, and appear to act via endothelial receptor tyrosine kinases (RTKs). At least four vascular endothelial growth factor subtypes have been identified.

Vascular endothelial growth factor (VEGF), now known as VEGF-A, has been isolated from several sources. VEGF-A shows highly specific mitogenic activity on endothelial cells, and can stimulate the whole sequence of events leading to angiogenesis. In addition, it has strong chemoattractant activity towards monocytes, can induce plasminogen activator and plasminogen activator inhibitor in endothelial cells, and can also influence microvascular permeability. Because of the latter activity, it is also sometimes referred to as vascular permeability factor (VPF). The isolation and properties of VEGF have been reviewed; see Ferrara et al., "The Vascular Endothelial Growth Factor Family of Polypeptides", *J. Cell. Biochem.*, 47: 211-218, 1991, and Connolly, "Vascular Permeability Factor: A Unique Regulator of Blood Vessel Function", *J. Cellular Biochem.*, 47: 219-223, 1991.

More recently, three further members of the VEGF family have been identified. These are designated VEGF-B, described in International Patent Application No. PCT/US96/02957 (WO 96/26736) by Ludwig Institute for Cancer Research and The University of Helsinki, VEGF-C, described in Joukov et al., *EMBO J.*, 1996 15: 290-298, and VEGF2, described in International Patent Application No. PCT/US94/05291 (WO 95/24473) by Human Genome Sciences, Inc. VEGF-B has closely similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique, screening for cellular proteins which might interact with cellular retinoic acid-binding protein type I (CRABP-I). Its isolation and characteristics are described in detail in PCT/US96/02597 and in Olofsson et al., *Proc. Natl. Acad. Sci.*, 1996 93: 2576-2581.

VEGF-C was isolated from conditioned media of PC-3 prostate adenocarcinoma cell line (CRL1435) by screening for ability of the medium to produce tyrosine phosphorylation of the endothelial cell-specific receptor tyrosine kinase Flt4, using cells transfected to express Flt-4. VEGF-C was purified using affinity chromatography with recombinant Flt-4, and was cloned from a PC-3 cDNA library. Its isolation and characteristics are described in detail in Joukov et al., *EMBO J.*, 15: 290-298, 1996.

VEGF-C is synthesized as a preproprotein in which the receptor binding VEGF homology domain (VHD) is flanked by amino- and carboxyl-terminal propeptides. Biosynthesis of the mature VHD involves proteolytic removal of the propeptides and results in greatly increased affinity of the VHD for VEGFR-2 and VEGFR-3 relative to the unprocessed, full length form (Joukov et al., (1997) *EMBO* 16: 3898-3911). Therefore, proteolytic processing activates VEGF-C. It has been suggested that VEGF-C may have a primary function in lymphatic endothelium, and a secondary function in angiogenesis and permeability regulation which is shared with VEGF (Joukov et al., *EMBO J.*, 1996 15: 290-298).

VEGF2 was isolated from a highly tumorgenic, estrogen-independent human breast cancer cell line. While this molecule is stated to have about 22% homology to PDGF and 30% homology to VEGF, the method of isolation of the gene encoding VEGF2 was unclear, and no characterization of the biological activity was disclosed.

Vascular endothelial growth factors appear to act by binding to receptor tyrosine kinases of the PDGF-receptor family. Five endothelial cell-specific receptor tyrosine kinases have been identified, namely Flt-1 (VEGFR-1), KDR/Flk-1 (VEGFR-2), Flt-4 (VEGFR-3), Tie, and Tek/Tie-2. All of these have the intrinsic tyrosine kinase activity necessary for signal transduction.

The specific role in vasculogenesis and angiogenesis of Flt-1, Flk-1, Tie, and Tek/Tie-2 has been demonstrated by targeted mutations inactivating these receptors in mouse embryos.

VEGFR-1 and VEGFR-2 bind VEGF with high affinity, and VEGFR-1 also binds VEGF-B and placenta growth factor (P1GF). VEGF-C has been shown to be the ligand for Flt-4 (VEGFR-3), and also activate VEGFR-2 (Joukov et al., *EMBO J.*, 15: 290-298, 1996) A ligand for Tek/Tie-2-has been described (International Patent Application No. PCT/US95/12935 (WO 96/112696) by Regeneron Pharmaceuticals Inc.) however, the ligand for Tie has not yet been identified.

The receptor Flt-4 is expressed in venous and lymphatic endothelia in the fetus, and predominantly in lymphatic endothelia in the adult (Kaipainen et al., *Cancer Res.*, 1994 54: 6571-6577; *Proc. Natl. Acad. Sci. USA*, 92: 3566-3570, 1995).

Vascular endothelial growth factor-D (VEGF-D) is a secreted glycoprotein that binds and activates VEGF receptor-2 (VEGFR-2) and VEGFR-3 (Achen et al., *Proc. Natl. Acad. Sci. USA* 95: 548-553, 1998), cell surface receptor tyrosine kinases expressed predominantly on blood vascular and lymphatic endothelia respectively (for review see Stacker et al., *FASEB J.* 16: 922-934, 2002). VEGFR-3 signals for lymphangiogenesis (growth of lymphatic vessels) (Veikkola et al., *EMBO J.* 20: 1223-1231, 2001) whereas VEGFR-2 is thought to signal for angiogenesis (growth of blood vessels). As would be expected given the receptor specificity of human VEGF-D, this growth factor stimulates both angiogenesis and lymphangiogenesis (1Byzova et al, *Blood* 99: 4434-4442, 2002; Veikkola et al, *EMBO J.* 20: 1223-1231, 2001; Marconcini et al., *Proc. Natl. Acad. Sci. USA* 96: 9671-9676, 1999)

Importantly, VEGF-D stimulated tumor angiogenesis that enhanced solid tumor growth and induced lymphangiogenesis that promoted metastatic spread of tumor cells to the lymphatics and lymph nodes (Stacker et al., *Nature Med.* 7: 186-191, 2001). Recently, VEGF-D expression was reported to be an independent prognostic factor for both overall and disease-free survival in colorectal cancer (White et al., *Cancer Res.* 62: 1669-1675, 2002).

VEGF-D is secreted from the cell in a relatively inactive form containing an N-terminal propeptide, a C-terminal propeptide, and a central VEGF homology domain ("VHD") containing the binding sites for VEGFR-2 and VEGFR-3 (Achen, M. G., M. Jeltsch, E. Kukk, T. Mäkinen, A. Vitali, A. F. Wilks, K. Alitalo, and S. A. Stacker. 1998. Vascular endothelial growth factor D (VEGF-D) is a ligand for the tyrosine kinases VEGF receptor 2 (Flk-1) and VEGF receptor 3 (Flt-4). Proc. Natl. Acad. Sci. USA95:548-553, Joukov, V., T. Sorsa, V. Kumnir, M. Jeltsch, L. Claesson-Welsh, Y Cao, O. Saksela, N. Kaikinen, and K. Alitalo. 1997. Proteolytic processing regulates receptor specificity and activity-of VEGF-C. EMBO J. 16:3898-3911, and Stacker et al., *J. Biol. Chem.* 274: 32127-32136, 1999.) Subsequently, the propeptides are proteolytically cleaved from the VHD to generate a mature form, consisting of dimers of the VHD, that binds VEGFR-2 and VEGFR-3 with high affinity. The affinities of the mature form for VEGFR-2 and VEGFR-3 are approximately 290-fold and 40-fold greater, respectively, than those of the unprocessed form (Stacker et al., 1999, supra).

Therefore, proteolytic processing of both VEGF-D and VEGF-C is a mechanism for activating the growth factors. The proteases involved in this activation process, however, were unknown. This activation may also be involved in various biological processes, including modulating protein localization, bioavailability, and receptor specificity. These processes, in turn, may be associated with various diseases. Selective inhibition and/or activation of these processes and activators thereof will provide treatment options for patients in need thereof.

A provisional matrix is known to play a key role in angiogenesis. The provisional matrix serves as substrate for adhesion, migration and invasion of endothelial cells, and is also essential for endothelial cell survival. The provisional matrix is continuously generated and broken down, a process known as remodeling, until a new vessel is properly formed.

Remodeling of the provisional matrix is highly regulated through the balanced action of numerous molecules. Plasmin, a serine protease formed through activation of its zymogen plasminogen, plays a key role by mediating degradation of the provisional matrix. Because of its critical role in the remodeling process of the provisional matrix, plasmin level is tightly controlled through an intricate coordination between plasminogen activators, plasminogen activator inhibitors and plasmin inhibitors, see e.g. International Patent Application WO 01/62799 A2.

SUMMARY OF THE INVENTION

The present invention for the first time identifies a protease capable of activating lymphangiogenic growth factors. In one embodiment, the present invention provides a method for activating at least one vascular endothelial growth factor selected from the group consisting of VEGF-C and VEGF-D, comprising treating said at least one vascular endothelial growth factor with a serine protease. Preferably, the serine protease is plasmin. The at least one vascular endothelial growth factor may be in an unprocessed form or a partially processed form.

In another embodiment, the present invention provides a method for screening for a protease that activates at least one of VEGF-C or VEGF-D, wherein said VEGF-D has at least one of a C-propeptide or an N-propeptide, the method comprising treating at least one of VEGF-C or VEGF-D with a candidate protease, and detecting VHD, wherein the detection of VHD indicates that the candidate protease is capable of activating VEGF-C or VEGF-D.

In a further embodiment, a method is provided for identifying inhibitors of activation of at least one VEGF-C or VEGF-D by plasmin. The method comprises admixing at least one of VEGF-C or VEGF-D with a candidate substance and plasmin, and measuring inhibition of release of VHD from the at least one of VEGF-C or VEGF-D. Preferably, the method further comprises testing whether said candidate substance inhibits degradation of another substrate of plasmin other than VEGF-C or VEGF-D, whereby a substance that inhibit release of VHD by plasmin but not degradation of the other substrate indicates that said substance is an inhibitor of activation of VEGF-C or VEGF-D. Inhibitors so identified merely inhibits the activation of VEGF-C or VEGF-D by plasmin, but do not otherwise affect the activity of plasmin on other substrates. While not wishing to be bound by any theory, it is believed that such inhibitors bind to VEGF-C or VEGF-D, thereby preventing the activation thereof by plasmin.

The present invention further provides a method of treatment, which method comprises administering to a patient in need thereof an effective amount of at least one inhibitor of plasmin. Preferably, the at least one inhibitor of VEGF-C or VEGF-D activation by plasmin does not other affect the activity of plasmin on other substrates. The inhibitor preferably is an antibody, or an immunologically active fragment thereof, to VEGF-C or VEGF-D.

The present invention additionally provides a method of treatment comprising administering to a patient in need thereof an effective amount of plasmin for activation of VEGF-C or VEGF-D, or both. Also provided is a pharmaceutical composition for activating VEGF-C or VEGF-D or both, the pharmaceutical composition comprising an effective amount of plasmin and a pharmaceutically acceptable excipient. Preferably, the method of treatment comprises administering an effective amount of the pharmaceutical composition to a patient in need thereof. Preferably, the method uses an antibody or fragment thereof wherein said antibody or fragment thereof binds to at least one of VEGF-D or VEGF-C, and wherein said antibody or fragment thereof blocks plasmin from activating at least one of VEGF-D or VEGF-C.

BRIEF DESCRIPTION OF THE DRAWINGS

FIG. 1 shows the scintillation proximity assay. FIG. 1A shows the sequence of the peptide encompassing the site at which the VHD of VEGF-D is cleaved from the C-terminal propeptide (C-pro). In VEGF-D from 293 EBNA cells cleavage occurs between arginine 205 and serine 206 (arrowhead) (Stacker, S. A., K Stenvers, C. Caesar, A. Vitali, T. Domagala, E. Nice, S. Roufail, R. J. Simpson, R. Moritz, T. Karpanen, K. Alitalo, and M. G. Achen. 1999. Biosynthesis of vascular endothelial growth factor-D involves proteolytic processing which generates non-covalent homodimers. J. Biol. Chem. 274:32127-32136). Numbers above the amino acid sequence denote positions in human VEGF-D (Achen, M. G, M Jeltsch, F. Kukk, T. Mkinen, A. Vali, A. F. Wilcs, K Alitalo, and S. A. Stacker. 1998. Vascular endothelial growth factor D (VEGF-D) is a ligand for the tyrosine kinases VEGF receptor 2 (Flk-1) and VEGF receptor 3 (Flt-4). Proc. Natl. Acad. Sci. USA 95:548-553). The C-terminal cysteine residue, not found in VEGF-D, facilitated radiolabeling. FIG. 1B shows the principle of SPA. Black bars represent biotinylated (B), tritiated VEGF-D peptide that is treated with proteases, then bound to streptavidin conjugated scintillant beads prior to .beta.-counting. SB denotes scintillant beads and open brackets denote streptavidin moieties conjugated to the beads. FIG. 1C shows the SPA results following treatment of VEGF-D peptide with proteases. Values are the average of three replicates ± one standard deviation and are representative of duplicate experiments. P values comparing plasmin- or thrombin-treated samples with negative control were calculated using Students' t test. Negative control is undigested peptide. FIG. 1D shows the mass spectrometric analysis of VEGF-D peptide before and FIG. 1E shows the mass spectrometric analysis of VEGF-D peptide after plasmin digestion. Identity of the major peak in FIGS. 1D and 1E is shown.

FIG. 2 shows proteolytic processing of VEGF-D by plasmin—Western blotting. FIG. 2A shows the analysis of human VEGF-D-FULL-N-FLAG (100 ng/lane) with anti-VHD antibody after digestion with 10, 1, 0.1 or 0 U/ml of plasmin. FIG. 2B shows α2-antiplasmin inhibition of plasmin. Plasmin (1 U/ml; 130 nM) was incubated with a range of α2-antiplasmin concentrations prior to addition of VEGF-D-FULL-N-FLAG and incubation at 37° C. for 1 hour. α2-antiplasmin:plasmin molar ratios are shown above the blot. FIG. 2C shows the analysis of mouse VEGF-D isoforms (100 ng/lane). Mouse VEGF-D$^{358}$ (358) and VEGF-D$^{326}$ (326) were treated with 1 U/ml plasmin (+) or left undigested (−). Sizes of molecular weight markers in kDa are shown to the left of each panel.

FIG. 3 shows that mature growth factors generated by plasmin bind and cross-link receptors. FIGS. 3B and 3C show the VFGFR-2/EpoR bioassays.

DETAILED DESCRIPTION OF THE INVENTION

Figure 3A:
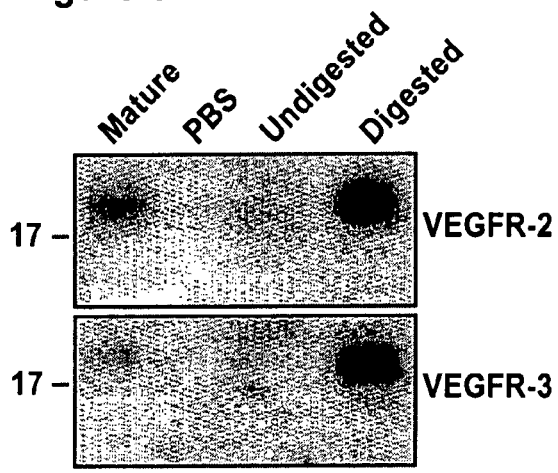
FIG. 3A shows binding to soluble receptors. Receptor-Ig fusion proteins containing the extracellular domains of human VEGFR-2 or VEGFR-3 were conjugated to protein-A sepharose and incubated with mature recombinant human VEGF-D as positive control (Mature), PBS as negative control, undigested and plasmin-digested full-length VEGF-D (Undigested and Digested, respectively). Upper, VEGFR-2 binding; Lower, VEGFR-3 binding. Material bound to the receptor-Ig proteins was analyzed by Western blotting using an anti-VHD antibody. Plasmin-generated mature VEGF-D (.about.21 kDa) is apparent. Sizes of molecular weight standards (kDa) are shown to the left.

The present invention provides a method for activating VEGF-C or VEGF-D, or both, using the protease plasmin. Furthermore, assays are disclosed for identifying inhibitors and activators of the proteolytic processing of VEGF-D and VEGF-C.

Previously, the protease(s) responsible for processing VEGF-D and VEGF-C were unknown. For the first time the present inventors found that the serine protease plasmin cleaves unprocessed and partially processed forms of VEGF-D and VEGF-C to generate the bioactive mature form thereof. In Example 2 below, the present inventors demonstrate in bioassays using both VEGFR-2 and VEGFR-3 that VEGF-C is likewise activated by plasmin.

This invention is the first disclosure that plasmin activates the lymphangiogenic growth factors VEGF-C and VEGF-D. Plasmin is also known to modulate the effects of the angiogenic protein VEGF. Plasmin cleaves some VEGF isoforms, releasing them from the extracellular matrix or cell surface thus making them available for inducing angiogenesis (Houck, K. A., D. W. Leung, A. M. Rowland, J. Winer, and N. Ferrara 1992. Dual regulation of vascular endothelial growth factor bioavailability by genetic and proteolytic mechanisms. J. Biol. Chem. 267:26031-26037, Plou ët, J., F. Moro, S. Bertagnolli, N. Coldeboeuf, H. Mazarguil, S. Clamens, and F. Bayard. 1997. Extracellular cleavage of the vascular endothelial growth factor 189-amino acid form by urokinase is required for its mitogenic effect. J. Biol. Chem. 272:13390-13396). In a porcine model of cutaneous wound healing, lymphatic vessels were observed to appear concurrently with blood vessels (Paavonen et al., 2000. Vascular endothelial growth factor receptor-3 in lymphangiogenesis in wound healing. Am. J. Pathol. 156:1499-1504) suggesting that angiogenesis and lymphangiogenesis are co-ordinately regulated. As VEGF-C and VEGF-D are localized on vascular smooth muscle in adult tissues (Achen, M. G, R. A. Williams, M. P. Minekus, G. E. Thornton, K. Stenvers, P. A. W. Rogers, F. Lederman, S. Roufail, and S. A. Stacker. 2001. Localization of vascular endothelial growth factor-D in malignant melanoma suggests a role in tumor angiogenesis. *J. Pathol.* 193:147-154, Partanen, T. A., J. Arola, A. Saaristo, L. Jussila, A. Ora, M. Miettinen, S. A. Stacker, M. G. Achen, and K. Alitalo. 2000. VEGF-C and VEGF-D expression in neuroendocrine cells and their receptor, VEGFR-3, in fenestrated blood vessels in human tissues. FASEB J. 14:2087-2096) and VEGF levels are elevated in cutaneous wounds,(Yao, F., S. Visovatti, C. S. Johnson, M. Chen, J. Slama, A. Wenger, and Eriksson. E. 2001. Age and growth factors in porcine fillthickness wound healing. *Wound Repair Regen.* 9:371-377), these growth factors are available to co-ordinate angiogenesis and lymphangiogenesis as a result of activation by plasmin during wound healing. Furthermore, plasmin degrades fibrin clots (Collen, D. and H. R Lijnen. 1991. Basic and clinical aspects of fibrinolysis and thrombolysis. *Blood* 78:3114-3124) and could therefore integrate fibrinolysis and vessel formation during wound healing.

Analysis of VEGF-D from mouse lung showed that only some, not all, of the VEGF-D was in the short ~21 kDa fully active form (Stacker, et al., J. Biol. Chem. 274:32127-32136, 1999). Accordingly, local administration of plasmin would increase VEGF-C or VEGF-D, or both (hereinafter "VEGF-C/D") activity in vivo because extra plasmin would convert the remaining full-length and partially processed growth factor to the fully active form, thereby increasing the total VEGF-C or -D activity in the tissues.

In a preferred embodiment, the present method of activating VEGF-C/VEGF-D is used for the treatment of lymphedema. In lymphedema, tissues swell due to inadequate lymphatic drainage as a result of damage to lymphatic vessels or lymph nodes. It is known that increased VEGF-C activity (via local delivery of VEGF-C protein) leads to growth of lympatics in lymphedematous tissue that helps to resolve lymphedema (Szuba et al., FASEB J. 16:1985-1987,2002).

VEGF-C and VEGF-D are known to induce angiogenesis (Byzova et al., Blood 99: 4434-4442, 2002; Cao et al., Proc. Natl. Acad. Sci. USA 95: 14389-14394, 1998). Accordingly, local administration of plasmin to activate these molecules and drive blood vessel growth could be used for treatment of diseases, such as ischemia.

Increased VEGF-C/D activity could be beneficial to induce repair of blood vessels to prevent restenosis after angioplasty performed on peripheral blood vessels or for treatment of coronary artery disease. Increased VEGF-C/D activity could also be beneficial to induce repair of blood vessels to prevent stenosis following transplantation of blood vessels for e.g. cardiac bypass therapy or for treatment of peripheral ischemia. Increased VEGF-C/D activity could further be beneficial to induce therapeutic angiogenesis or arteriogenesis for treatment of ischemic heart disease and other diseases of ischemia including peripheral tissue ischemia Therefore, according to another embodiment of the present invention, plasmin activation of VEGF-C/D is inhibited using ligand-binding molecules that block interaction with the processing protease(s). According to the present invention, substances that can bind VEGF-C/D can be used to block activation of these growth factors. These activation-blocking substances can be used to treat diseases such as cancer. Preferably, the cancers to be treated are those in which VEGF-C or VEGF-D induces tumor lymphangiogenesis that drives metastatic spread of tumor cells via the lymphatics (Stacker et al., Nature Med. 7:186-191, 2001; Skobe et al., Nature Med. 7: 192-198, 2001; Mandriota et al., EMBO J. 20: 672-682, 2001). Therefore inhibition of these growth factors constitutes an anti-metastatic approach to cancer therapeutics. VEGF-C/D also induce tumor angiogenesis that stimulates growth of solid tumors (Stacker et al., Nature Med. 7:186-191, 2001) so inhibition would be beneficial from this perspective also.

Others diseases that can be treated by inhibition of VEGF-C/D include lymphangioma, lymphangiosarcoma, and diseases involving uncontrolled angiogenesis such as diabetic retinopathy and arthritis. Inhibition of VEGF-C/D can also prevent ocular neovascularization, which is characterized by invasion of new blood vessels into the structures of the eye such as the retina or cornea. It is the most common cause of blindness and is involved in approximately twenty eye diseases, such as diabetic retinopathy and advanced age-related macular degeneration. In advanced age-related macular degeneration, the associated visual problems are caused by an ingrowth of chorioidal capillaries through defects in Bruch's membrane with proliferation of fibrovascular tissue beneath the retinal pigment epithelium.

Preferably, an anti-VEGF-D antibody that blocked the binding of VEGF-D to VEGFR-2 and VEGFR-3 may be administered to a patient in need of the inhibition of VEGF-C/D. In another embodiment, the soluble extracellular domain of VEGFR-3 may be used to sequester VEGF-C and VEGF-D, achieving an inhibition effect. Studies in animal models showed that inhibiting the VEGFR-3 signaling pathway blocked tumor lymphangiogenesis and metastasis via the lymphatics (Stacker, S. A., C. Caesar, M. E. Baldwin, G. E. Thornton, R. A. Williams, R. Prevo, D. G. Jackson, S. -I. Nishikawa, H. Kubo, and M. G Achen. 2001. VEGF-D promotes the metastatic spread of tumor cells via the lymphatics. *Nat. Med.* 7:186-191, He, Y., K. Kozaki, T. Karpanen, K. Koshikawa, S. Yla-Herttuala, T. Takahashi, and K. Alitalo. 2002. Suppression of tumor lymphangiogenesis and lymph node metastasis by blocking vascular endothelial growth factor receptor 3 signaling. *J. Natl. Cancer Inst.* 94:819-825).

Clinical studies revealed that expression of VEGF-D in breast, ovarian and colorectal cancer may be an independent prognostic indicator of survival associated with lymph node metastasis (Yokoyama, Y., D. S. Charnock-Jones, D. Licence, A. Yanaihara, J. M. Hastings, C. M. Holland, M. Emote, M. Umemoto, T. Sakamoto, S. Sato, H. Mizunuma, and S. K. Smith. 2003. Vascular endothelial growth factor-D is an independent prognostic factor in epithelial ovarian carcinoma. *Br. J. Cancer* 88:237-244, White, J. D., P. W. Hewett, D. Kosuge, T. McCulloch, B. C. Enhoim, J. Carmichael, and J. C. Murray. 2002. Vascular endothelial growth factor-D expression is an independent prognostic marker for survival in colorectal carcinoma. *Cancer Res.* 62:1669-1675, Nakamura, Y., H. Yasuoka, M. Tsujimoto, Q. Yang, S. Imabun, M. Nakahara, K. Nakao, M. Nakamura, I. Mori, and K. Kakudo. 2003. Prognostic significance of vascular endothelial growth factor D in breast carcinoma with long-term follow-up. *Clin. Cancer Res.* 9:716-721). Moreover, expression of lymphangiogenic growth factors promoted metastatic spread of tumor cells via the lymphatics in animal models (Stacker, S. A., C. Caesar, M. E. Baldwin, G. E. Thornton, R. A. Williams, R. Prevo, D. G. Jackson, S. -I. Nishikawa, H. Kubo, and M. G. Achen. 2001. VEGF-D promotes the metastatic spread of tumor cells via the lymphatics. *Nat. Med.* 7:186-191, Mandriota, S. J., L. Jussila, M. Jeltsch, A. Compagni, D. Baetens, R. Prevo, S. Banejji, J. Huarte, R. Montesano, D. G. Jackson, L. Orci, K. Alitalo, G. Christofori, and M. S. Pepper. 2001. Vascular endothelial growth factor-C-mediated lymphangiogenesis promotes tumor metastasis. EMBO J. 20:672-682, Skobe, M., T. Hawighorst, D. G. Jackson, R. Prevo, L. Janes, P. Velasco, L. Riccardi, K. Alitalo, K. Claffey, and M. Detmar. 2001. Induction of tumor lymphangiogenesis by VEGF-C promotes breast cancer metastasis. *Nat. Med.* 7:192-198). Plasmin and other members of the fibrinolytic system have also been associated with tumor growth and metastasis (for review see (Andreasen, P. A., R. Egelund, and H. H. Petersen. 2000. The plasminogen activation system in tumor growth, invasion, and metastasis. *Cell. Mol. Life Sci.* 57:25-40)) as shown in models in which the fibrinolytic system was manipulated. For example, overexpression of plasminogen activator inhibitor-2 inhibited the metastasis of a human melanoma cell line to both the lymph nodes and the lung (Mueller, B. M., Y. B. Yu, and W. E. Laug. 1995. Overexpression of plasminogen activator inhibitor 2 in human melanoma cells inhibits spontaneous metastasis in scid/scid mice. *Proc. Natl. Acad. Sci. USA.* 92:205-209). Furthermore, plasminogen-null mice displayed fewer regional lymph node metastases than controls when transplanted with Lewis lung carcinoma (Bugge, T. H., K. W. Kombrinck, Q. Xiao, K. Holmback, C. C. Daugherty, D. P. Witte, and J. L. Degen. 1997. Growth and dissemination of Lewis lung carcinoma in plasminogen-deficient mice. *Blood* 90:4522-4531). A contributing factor underlying these observations could be that down regulation of plasmin production leads to diminished tumor lymphangiogenesis and metastasis via the lymphatics.

In a preferred embodiment, the activation blocking substance is an antibody against VEGF-C/D.

In a further embodiment, methods are provided for screening for inhibitors that specifically block the action of plasmin on VEGF-C and VEGF-D. Inhibition of VEGF-C/D activation may be achieved by plasmin or other serine protease inhibitors. Plasmin, however, is known to cleave many other proteins, (including VEGF-A and fibrin clots). Thus a general plasmin inhibitor may not be very useful due to a potential wide range of side effects. In contrast, inhibitors that only block plasmin's capacity to activate VEGF-C and VEGF-D would be much more useful to specifically block tumor lymphangiogenesis and angiogenesis.

The screening methods of the present invention identify such inhibitors. In one embodiment, such inhibitors may bind to VEGF-C/D, which binding prevents the interaction with plasmin, leading to the inhibition of VEGF-C/D activation by plasmin, but not interfering with plasmin's capacity to cleave proteins unrelated to VEGF-C/D, such as the remodeling of the provisional matrix.

As used herein, the term "VEGF-D" collectively refers to vascular endothelial growth factor D, as well as fragments or analogs thereof which have the biological activity of VEGF-D as herein defined, and as known in the art. Examples of biological activity include, for example, receptor binding and endothelial cell proliferation.

As used herein, the term "VEGF-C" collectively refers to vascular endothelial growth factor C, as well as fragments or analogs thereof which have the biological activity of VEGF-C as herein defined, and as known in the art. Examples of biological activity include, for example, receptor binding and endothelial cell proliferation.

As used herein, the term "antibodies and fragments thereof" includes any and all biologically active portions or complete antibodies, including but not limited to Fab, Fab2, Fscv, Fab', etc. Descriptions of antibody types and fragments thereof may be found in any immunology textbook, e.g., Paul, *Fundamental Immunology*.

EXAMPLES

Example 1

Materials and Methods

Peptide Labeling.

One milligram of biotinylated peptide (Auspep, Parkville, Australia) in 200 µl of 200 mM 2-morpholinoethanesulfonic acid (UES), pH 6.0, was mixed with 455 µCi of [$^3$H] Nethyl-maleimide (NEM) in pentane (Perkin Elmer Lifesciences, Boston, Mass.), and pentane removed under $N_2$. After incubation at room temperature (RT) for 10 min, 50 µg of NEM in 200 mM MES, pH 6.0, was added and incubated for one hour at RT. A further 500 µg of NEM in 200 mM MES, pH 6.0, was added and incubated for one hour at RT. Labelled peptide was separated from unincorporated label by chromatography on Sephadex G-10 in 150 mM NaCl.

Purification of VEGF-C and VEGF-D.

VEGF-C-FULL-N-FLAG or VEGF-D-FULL-N-FLAG (full-length human VEGF-C or VEGF-D tagged at the N-terminus with the FLAG octapeptide), VEGF-DΔNΔCFLAG (the VHD of human VEGF-D tagged at the N-terminus with FLAG) (Stacker, S. A., K. Stenvers, C. Caesar, A. Vitali, T. Domagala, E. Nice, S. Roufail, R. J. Simpson, R. Moritz, T. Karpanen, K. Alitalo, and M. G. Achen. 1999. Biosynthesis of vascular endothelial growth factor-D involves proteolytic processing which generates non-covalent homodimers. *J. Biol. Chem.* 274:32127-32136) and mouse VEGF-$D_{326}$-FLAG and VEGF-$D_{358}$-FLAG (full-length isoforms tagged at the C-termini with FLAG) (Baldwin, M. E., S. Roufail, M. M. Halford, K. Alitalo, S. A. Stacker, and M. G. Achen. 2001. Multiple forms of mouse vascular endothelial growth factor-D are generated by RNA splicing and proteolysis. *J. Biol. Chem.* 276:44307-44314) were purified from the conditioned media of transfected 293EBNA cells as described.

Protease Digests.

Protease digestions were in 10 mM potassium phosphate buffer, pH 7.5, 150 mM NaCl at 37° C. for one hour. Digests contained between 10 and $10^2$ U/ml of plasmin from human serum (Calbiochem, San Diego, Calif.). α2-antiplasmin (Calbiochem) was incubated with plasmin in PBS for 30 min at RT before addition of VEGF-D-FULL-N-FLAG and digestion at 37° C. for one hour. Digests with tissue plasminogen activator (Calbiochem) contained 0.5 to 50 kU/ml of enzyme. Scintillation proximity assays contained plasmin (0.1 U/ml), thrombin (0.1 U/ml), MMP-2 (5 mU/ml) or MMP-9 (9 mU/ml) (Calbiochem).

Scintillation Proximity Assay.

After incubation with proteases, $10^4$ cpm of labelled biotinylated peptide was mixed with 200 mg of streptavidin scintillant beads (Amersham Biosciences, Uppsala, Sweden) in 10 mM potassium phosphate buffer, pH 6.0, at RT for 20 min, before β-counting.

Western Blotting.

After SDS-PAGE and transfer to membranes, proteins were probed with biotinylated antibody to the VHD of mouse VEGF-D (R & D Systems, Minneapolis, Minn.) and HRP-conjugated streptavidin (Zymed Laboratories, San Francisco, Calif.) and developed using chemiluminescence (Pierce Biotechnology, Rockford, Ill.).

Amino Acid Sequencing.

N-terminal amino acid sequencing was with a biphasic NH2-terminal protein sequencer (Model G1005A, Agilent Technologies, Palo Alto, Calif.).

Mass Spectrometry.

Peptides were desalted using $\mu C_{18}$ ZipTips (Millipore, Bedford, Mass.) and co-crystallized onto a 10×10 MALDI stainless steel sample plate (Applied Biosystems, Foster City, Calif.) with 2,5-dihydroxy benzoic acid matrix (Agilent Technologies) in 0.1% TFA/60% acetonitrile and dried for 10 min. Samples were analyzed on the o-MALDI QStar™ Pulsar mass spectrometer (Applied Biosystems). Positive TOF MS was collected from 700 to 3000 Da for one min.

Assays of Receptor Binding and Cross-linking.

Binding assays with VEGF-D-FULL-N-FLAG and soluble receptor-Ig fusion proteins containing the extracellular domains of human VEGFR-2 or VEGFR-3 and the Fc portion of human IgG[1] (Y. Gunji, Haartman Institute and K. Pajusola, Biotechnology Institute, Helsinki, respectively) were carried out as described previously as were bioassays with Ba/F3 cells and ligands at 750 ng/ml (Achen et al., 1998, Proc. Natl. Acad. Sci. USA 95: 548-553).

Example 1

Assay for VEGF-D Processing.

To identify proteases that activate VEGF-D, a scintillation proximity assay (SPA) was developed for monitoring cleavage of the C-terminal propeptide from the VHD. The assay was based on the C-terminal cleavage because this occurs at a single site in VEGF-D whereas cleavage of the N-terminal propeptide is more complex, occurring at two distinct sites (Stacker, et al., 1999, Biosynthesis of vascular endothelial growth factor-D involves proteolytic processing which generates non-covalent homodimers, J. Biol. Chem274:32127-32136). For the assay, a 17-mer peptide (containing residues 198 to 213 of human VEGF-D) spanning the C-terminal cleavage site of VEGf-D, was biotinylated at its N-terminus and radiolabeled at its C-terminus (FIG. 1A). The principle of the SPA is outlined in FIG. 1B. After the peptide is treated with proteases, it is bound to streptavidin-conjugated beads impregnated with scintillant. When the peptide is intact, the proximity of the radiolabel at the C-terminus of the peptide to the scintillant in the beads is sufficient to generate detectable photons. In contrast, there is a dramatic reduction in counts detected when cleavage of the peptide has occurred because the radiolabel is no longer sufficiently close to the scintillant for photons to be generated.

A range of proteases were tested in this assay, including plasmin, thrombin and matrix metalloproteinase-2 (MMP-2) and MMP-9. These proteases were chosen because of their involvement in angiogenesis or tumor formation. MMP-2 and MMP-9 had no effect on the counts detected in the SPA, however, plasmin caused a greater than 90% reduction of signal, indicating substantial cleavage of the peptide (FIG. 1C).—Thrombin caused a small reduction of signal. To identify the site(s) at which plasmin hydrolysed the peptide, samples were analysed by mass pectrometry. Undigested peptide consisted of a single peak of molecular mass 2282.15, as expected (FIG. 1D). Following plasmin treatment, a predominant peak of molecular mass 1267.68 was observed, corresponding to Biotin-HYSIIRR (FIG. 1E). This molecular species is an expected product of cleavage of the peptide at the same site as observed in VEGF-D expressed in 293EBNA cells, i.e. between R205 and S206 (FIG. 1A) (Stacker et al., 1999, J. Biol. Chem. 274:32127-32136). An alternative cleavage event generating Biotin-HPYSIIR (molecular mass 1111.59) was also detected.

Example 2

Plasmin Processes VEGF-D

To establish if VEGF-D is a substrate for plasmin, this protease was incubated with full-length human VEGF-D (VEGF-D-FULL-N-FLAG) purified from the medium of transfected 293EBNA cells. A degree of proteolytic processing occurs in the medium of these cells resulting in VEGF-D preparations containing full-length material (~50 kDa) and a partially processed form (~31 kDa) consisting of the N-terminal propeptide and VHD (FIG. 2A) (Stacker, S. A., K. Stenvers, C. Caesar, A. Vitali, T. Domagala, E. Nice, S. Roufail, R. J. Simpson, R. Moritz, T. Karpanen, K. Alitalo, and M. G. Achen. 1999. Biosynthesis of vascular endothelial growth factor-D involves proteolytic processing which generates non-covalent homodimers. J. Biol. Chem. 274:32127-32136). After plasmin digestion, a single ~21 kDa band was detected by Western blotting (FIG. 2A).This species corresponds to the previously observed mature, fully-processed form of VEGF-D, suggesting that plasmin can cleave both the N-and C-terminal propeptides from the VHD. N-terminal amino acid sequencing of this ~21 kDa species revealed two sequences, FAATFYDIE and VIDEE, indicating that cleavage of the N-terminal propeptide was occurring at two sites. FAATF (residues 89 to 93 of VEGF-D) represents the sequence identified as the N-terminus of the predominant form of fully processed, mature VEGF-D purified from the conditioned medium of 293EBNA cells. VIDEE (residues 101 to 105 of VEGF-D) represents an N-terminus that is located one residue towards the C-terminus compared with that of the other form of mature VEGF-D (KVIDEE) detected in the medium of 293EBNA cells (Stacker, S. A., K. Stenvers, C. Caesar, A. Vitali, T. Domagala, E. Nice, S. Roufail, R. J. Simpson, R. Moritz, T. Karpanen, K. Alitalo, and M. G Achen. 1999. Biosynthesis of vascular endothelial growth factor-D involves proteolytic processing which generates non-covalent homodimers. J. Biol. Chem. 274:32127-32136). Therefore, plasmin cleaves the N-terminal propeptide from the VHD at almost identical positions to those described previously. In contrast to plasmin, the serine proteases thrombin and tissue plasminogen activator were unable to cleave the propeptides of human VEGF-D from the VHD (data not shown).

The plasmin used in this study was purified from human plasma. In order to eliminate the possibility that the processing of VEGF-D observed was due to a contaminating activity in the plasmin preparation, α2-antiplasmin, a specific inhibitor of plasmin that forms an inactive 1:1 complex with this protease (Collen at al., 1991, *Blood* 78:3114-3124)), was incubated with the plasmin sample before digestion of VEGF-D. Analysis of resulting digestion products demonstrated complete inhibition of digestion by α2-antiplasmin when included at a 5-fold molar excess to plasmin (FIG. 2B). Therefore, the observed proteolytic processing of VEGF-D by the plasmin preparation used here was due to plasmin.

Full-length mouse VEGF-D exists as two isoforms, VEGF-$D_{326}$ and VEGF-$D_{358}$, that differ in the C-terminus of the protein (Baldwin et al., 2001, J. Biol. Chem. 276:44307-44314). Plasmin digestion of the mouse VEGF-D isoforms was carried out to analyze the effect of the distinct C-termini on proteolytic processing. Plasmin treatment of both isoforms produced a ~1 kDa species containing the VHD, as for human VEGF-D, indicating that this enzyme can fully process both isoforms (FIG. 2C).

Example 3

Plasmin Generates Bioactive VEGF-D and VEGF-C

In order to establish if mature VEGF-D generated by plasmin binds VEGFR-2 and VEGFR-3 we carried out immuno precipitation studies using soluble receptor-Ig fusion proteins containing the extracellular domains of VEGFR-2 or VEGFR-3 (FIG. 3a). This revealed that the plasmin-generated mature forms bound to both VEGFR-2 and VEGFR-3 extracellular domains.

Figure 3B:
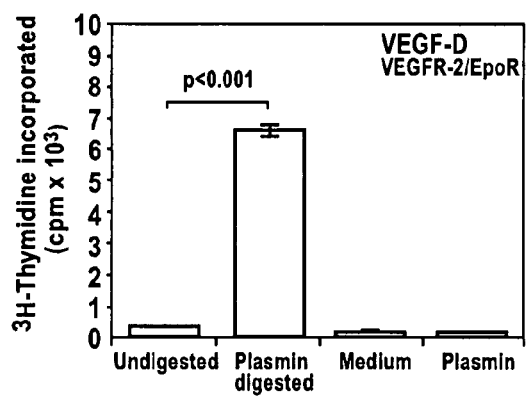
FIGS. 3B and 3C show the analysis of receptor binding and cross-linking in BaF3 bioassays. Ba/F3 cells expressing chimeric receptors containing the extracellular domains of VEGFR-2 or VEGFR-3 and the cytoplasmic domain of EpoR were treated with plasmin-digested or undigested full-length VEGF-D (FIG. 3B) or VEGF-C (FIG. 3C).
Figure 3C:
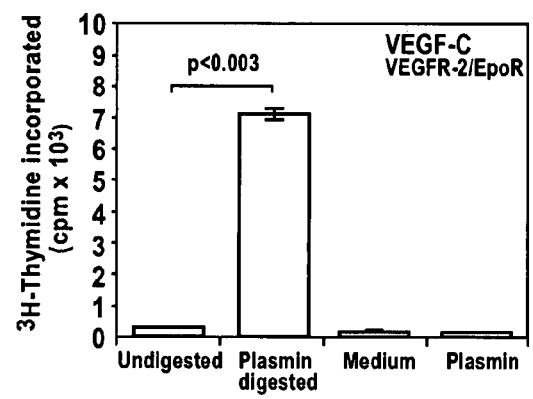
Figure 3D:
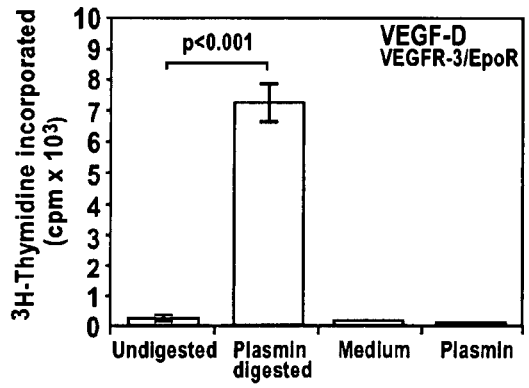
FIGS. 3D and 3E show the VEGFR-3/EpoR bioassays. Controls were medium lacking growth factor (Medium) or plasmin digests lacking growth factor (Plasmin). Values are the average of duplicates ± one standard deviation and are representative of three experiments. P values comparing results of plasmin-digested with undigested material were calculated using Students' t test.
Figure 3E:
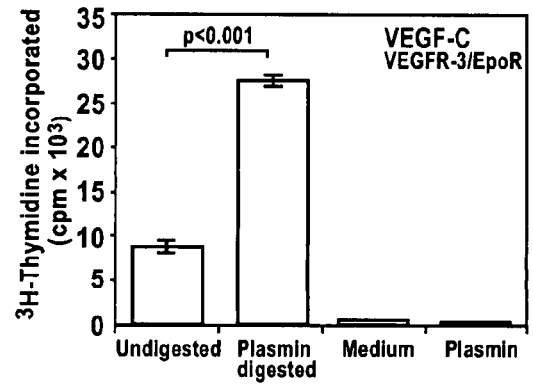

To compare the capacities of full-length and plasmin-generated mature VEGP-D to bind and cross-link receptors at the cell surface, bioassays were employed utilizing Ba/F3pre-B cells expressing chimeric receptors consisting of the extracellular domains of human VEGFR-2 or VEGFR-3 and the transmembrane and cytoplasmic domains of the eryturopoietin receptor (EpoR) (Stacker, et al., 1999, A mutant form of vascular endothelial growth factor (VEGF) that lacks VEGF receptor-2 activation retains the ability to induce vascular permeability, J. Biol. Chem. 274:34884-34892; Achen, et al., 2000, Monoclonal antibodies to vascular endothelial growth factor-D block interactions with both VEGF receptor-2 and VEGF receptor-3, Fur. J. Biochem. 267:2505-2515). These cell lines are IL-3 -dependent, however, signaling from the EpoR cytoplasmic domain, that occurs when the extracellular domains of the chimeric receptors are cross-linked by ligand, leads to cell survival and proliferation in the absence of IL-3. These bioassays allow comparison of receptor binding and cross-linking and were used to define the receptor interactions of a range of VEGFR-2 and VEGFR-3 ligands (Achen, et al., 1998, Vascular endothelial growth factor D (VEGF-D) is a ligand for the tyrosine kinases VEGF receptor 2 (Flk-1) and VEGF receptor 3 (Flt-4), Proc. Natl. Acad. Sci. USA 95:548-553; Stacker, et al., 1999, A mutant form of vascular endothelial growth factor (VEGF) that lacks VEGF receptor-2 activation retains the ability to induce vascular permeability, J. Biol. Chem. 274:34884-34892; Achen, et al., 2000, Monoclonal antibodies to vascular endothelial growth factor-D block interactions with both VEGF receptor-2 and VEGF receptor-3, Eur. J. Biochem 267:2505-2515; Wise, et al., 1999, Vascular endothelial growth factor (VEGF)like protein from orf virus NZ2 binds to VEGFR2 and neuropilin-1, Proc. Natl. Acad. Sci. USA 96:3071-3076). Cells were incubated with undigested or plasmin digested VEGF-D in the absence of IL-3 and the proliferative response assessed by incorporation of [$^3$H]thymidine into DNA. Cells expressing either the VEGFR-2 or VEGFR-3 chimeric receptors, that were exposed to plasmin-digested VEGF-D, exhibited a much greater response than those treated with undigested protein (FIG. 3B). Therefore, plasmin treatment generates mature forms of VEGF-D that are much better able to bind and cross-link VEGFR-2 and VEGFR-3 at the cell surface than full-length material. Comparable results were observed with VEGF-C, (FIG. 3C), indicating that plasmin activates both of the known lymphangiogenic growth factors.

Example 5

Plasmin Liberates Mature VEGF-D

The plasmid pEFBOS-SS-Myc-VEGF-$D_{358}$-FLAG, encoding full-length mouse VEGF-$D_{358}$ tagged at the N-terminus with two Myc epitopes and at the C-terminus with the FLAG octapeptide (Baldwin et al., J. Biol. Chem., 47: 44307-44314, 2001), was used to transiently transfect 293EBNA cells using Fugene according to manufacturer's instructions. Mouse VEGF-$D_{358}$ was purified from the conditioned cell culture medium by affinity chromatography using anti-FLAG monoclonal antibody M2 (Sigma) according to the manufacturer. Purified mouse VEGF-D (100 ng) was incubated with 0, $1\times10^{-4}$, $1\times10^{-5}$, $1\times10^{-6}$ and $1\times10^{-7}$ units of plasmin (Calbiochem) at 37° C. for one hour in 10 mM potassium phosphate, 150 mM NaCl, pH 7.5. As control, mouse VEGF-D was incubated with zero, $1\times10^{-4}$, $1\times10^{-5}$, $1\times10^{-6}$ and $1\times10^{-7}$ units of thrombin (Calbiochem) at 37° C. for one hour.

Figure 4:
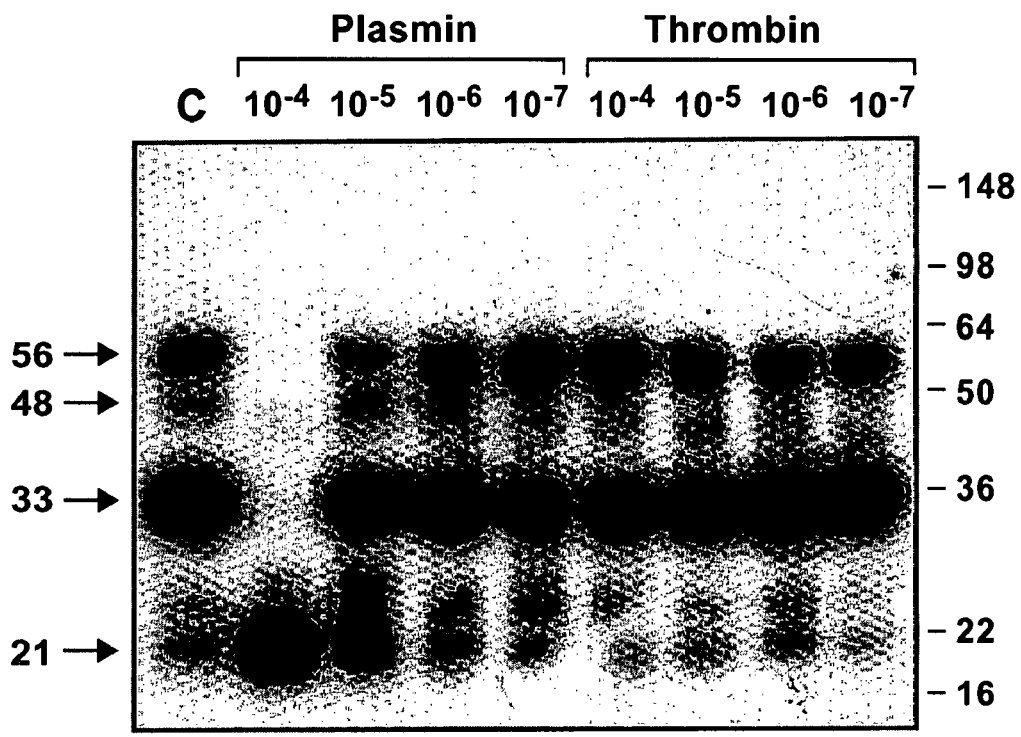
FIG. 4 shows a Western blot analysis of mouse VEGF-D$_{358}$ (100 ng) digested with varying amounts of plasmin or thrombin. Numbers at the top of each lane denote the units of protease included in each incubation. "C" denotes negative control for which proteases were omitted from the incubation. Numbers and arrows to the left denote molecular species of VEGF-D and those to the right the positions of molecular weight markers.

The resulting material was analyzed by Western blot using biotinylated antibodies against the VHD of VEGF-D (R & D Systems) and streptavidin-horseradish peroxidase conjugate (Zymed). The results of the Western blot analysis are shown in FIG. 4. The abundant bands in the control sample (i.e., sample that was not incubated with protease; lane C) have been characterized previously (Stacker et al., J. Biol. Chem. 274: 32127-32136, 1999) and are as follows: the 56 kDa band is full-length VEGF-D, the 48 kDa band consists of the VHD bound to the C-terminal propeptide, the 33 kDa species is the VHD bound to the N-terminal propeptide and the 21 kDa band is the mature VEGF-D subunit. Incubation with plasmin profoundly altered the relative abundance of these species. When $1\times10^{-4}$ units of plasmin were included in the incubation, all species other that the mature form became virtually undetectable whereas the mature form (21 kDa) increased dramatically in abundance (FIG. 4, plasmin lane $10^{-4}$).

This indicates that plasmin proteolytically released the VHD from full-length material and both of the partially processed forms. This effect was dose-dependent as, in comparison to the result with $1\times10^{-4}$ units, the VHD became less abundant and the other species more abundant with decreasing concentrations of plasmin (FIG. 4, plasmin lanes $10^{-5}$ to $10^{-7}$). In contrast, the effect of thrombin was marginal at best, even at the highest concentration of enzyme (FIG. 4., thrombin lanes $10^{-4}$ to $10^{-7}$). These results demonstrate that plasmin activates VEGF-D as it can liberate mature VEGF-D from unprocessed and partially processed forms.

Example 6

Assay for Inhibitors of VEGF-D Processing

In order to establish an approach to screen for inhibitors of VEGF-D processing we developed a scintillation proximity assay ("SPA") to detect cleavage of the C-terminal propeptide of VEGF-D from the VHD. A peptide of the following amino acid sequence was synthesized by standard methods, containing a biotin moiety (bio) at the N-terminus:

bio-His-Pro-Tyr-Ser-Ile-Ile-Arg-Arg-Ser-Ile-Gln-Ilo-Pro-Glu-Glu-Asp-Cys (SEQ ID NO: 1).

Residues 1-16 of this peptide correspond to residues 198 to 213 of human VEGF-D (Achen et al., Proc. Natl. Acad. Sci. USA 95: 548-553, 1998) and cleavage of the VHD from the C-terminal propeptide occurs immediately after the C-terminal arginine in the sequence of the peptide (Stacker et al., J. Biol Chem. 274: 32127-32136, 1999). The peptide was radiolabelled at the C-terminus by reaction with ethyl maleimide, N-[ethyl-1,2-$^3$H] (Perkin Elmer) (Brown et al., Anal Biochem. 217: 139-147, 1994).

Radiolabelled peptide was incubated with plasmin (zero, 0.001, 0.005 and 0.01 units) (Calbiochem) or with thrombin (0.001, 0.005 and 0.01 units) (Calbiochem) in 10 mM potassium phosphate, 150 mM NaCl, pH 7.5, in a total volume of 10 µl in eppendorf tubes at 37° C. for one hour. Subsequently the products were incubated with streptavidin-conjugated scintillant beads (Amersham Pharmacia) for 20 min in eppendorf tubes, and the entire reaction was transferred to a Unifilter 96-well plate and counted using a Topcount NXT Microplate scintillation counter (Packard).

The basis of the SPA is that the radiolabel at the C-terminus of the peptide is only detected by β-counting if it is in very close proximity to the scintillant in the beads. This, in turn, only occurs if the peptide is bound to a streptavidin moiety on a scintillant bead (via the N-terminal biotin moiety of the peptide) and if the peptide is still intact (i.e., if the C-terminal radiolabel has not been separated from the N-terminal biotin moiety due to proteolysis). In contrast, proteolytic cleavage of the peptide ensures that the C-terminal radiolabel is not close enough to the scintillant in the bead to allow detection by β-counting.

In summary, proteolytic cleavage of the peptide at the site where the VHD of VEGF-D is cleaved from the C-terminal propeptide will result in a dramatic decrease in counts detected. The results of the assay carried out in the presence of various amounts of plasmin or thrombin are shown in Table 1. Clearly, plasmin cleaved the radiolabelled peptide at all concentrations tested, as indicated by decreases in counts detected, whereas thrombin did not. These results are consistent with those observed by Western blot analysis previously discussed.

The SPA described herein will be used for large-scale screening for inhibitors of the cleavage of the VHD of VEGF-D from the C-terminal propeptide. Examples of such inhibitors of interest in a screening method will be, for example, small molecules, antibodies, or peptidomimetics. The assay, or method, will be used to identify inhibitors of plasmin or inhibitors of any other protease or proteases that are capable of carrying out this cleavage event.

The SPA was initially completed using C-terminal propeptide cleavage, however, this method and assay system may be slightly modified and will also be used to identify inhibitors of the cleavage of the VHD from the N-termninal propeptide of VEGF-D. In addition, these methods may also be applicable to other members of the VEGF family, such as, for example, VEGF-C.

Table 1 shows the results of the scintillation proximity assay for proteolysis at the junction of the VHD and C-terminal propeptide of VEGF-D.

TABLE 1

|  |  | Plasmin (units) | | | Thrombin (units) | | |
| --- | --- | --- | --- | --- | --- | --- | --- |
| Enzyme: | None | 0.001 | 0.005 | 0.01 | 0.001 | 0.005 | 0.01 |
| Counts/min | 9367 | 414 | 217 | 118 | 8331 | 8984 | 8924 |

Example 7

Plasmin Activation of VEGF-C

A bioassay for binding and cross-linking of VEGFR-2 and VEGFR-3 was developed in the interleukin-3 (IL-3) dependent Ba/F3 pre-B cell line (see patent applications PCT/US95/16755 and PCT/US97/14696; Achen et al., (2000) *Eur. J. Biochem.* 267, 2505-2515; Stacker et al., (1999) *J. Biol. Chem.* 274: 34884-34892). In the absence of IL-3, Ba/F3 cells die within 48hrs. Cell lines were derived from the Ba/F3 line expressing chimeric receptors consisting of the extracellular domain of VEGFR-2 or VEGFR-3 and the transmembrane and cytoplasmic domains of the erythropoietin receptor (EpoR). Cross-linking of the extracellular domains of the chimeric receptors by dimeric ligands (e.g. VEGF-C or VEGF-D) induces signaling via the cytoplasmic EpoR domain resulting in cell survival and proliferation. Therefore, activating ligands of VEGFR-2 and VEGFR-3 promote survival of these cell lines in the absence of IL-3.

Human recombinant full-length VEGF-C, tagged at the N-terminus with the FLAG octapeptide, was purified by anti-FLAG affinity chromatography from the conditioned culture medium of 293EBNA-cells following transient transfection with plasmid pEFBOS-S-FLAG-hVEGF-C-Full, a derivative of pEFBOS-S-FLAG (Stacker et al.(1999) *J. Biol. Chem.* 274: 32127-32136) in which the coding region of FLAG-tagged full-length human VEGF-C is under the control of the elongation factor-1α gene promoter. VEGF-C was digested with plasmin from human serum ($1 \times 10^{-3}$U, Calbiochem) at 37° C. for one hour in PBS.

The Ba/F3 cells expressing either the VEGFR-2/EpoR or VEGFR-3/EpoR chimeric receptors were washed thrice in PBS, once in media lacking IL-3 and resuspended at a concentration of $7.4 \times 10^4$ cells/ml in media lacking IL-3. Approximately 10,000 cells (135 µl) were aliquoted/well of a 96 well cell culture plate. To each well was added either 250 ng of undigested full-length VEGF-C, 250 ng of plasmin-digested VEGF-C or a negative control consisting of 15 µl of medium lacking IL-3. Following 48 hrs incubation at 37° C. in 10% $CO_2$ environment, 1 µCi of [$^3$H] thymidine was added to each well, and the cells incubated for 4 hours. Cells were then harvested, and viability assayed by scintillation counting.

Figure 5A:
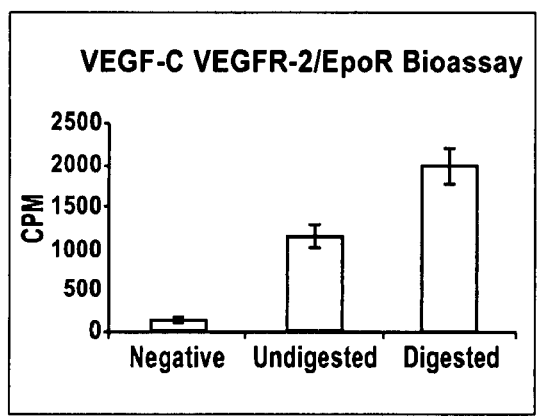
FIG. 5 shows both a VEGFR-2 bioassay (FIG. 5A) and a VEGFR-3 bioassay (FIG. 5B) with VEGF-C. Results with undigested full-length VEGF-C and material digested with plasmin are shown. VEGF-C was omitted to show the negative control. Values are the average of three replicates ± 1 standard deviation. P values for comparison of digested with undigested samples were calculated using Students' t test.
Figure 5B:
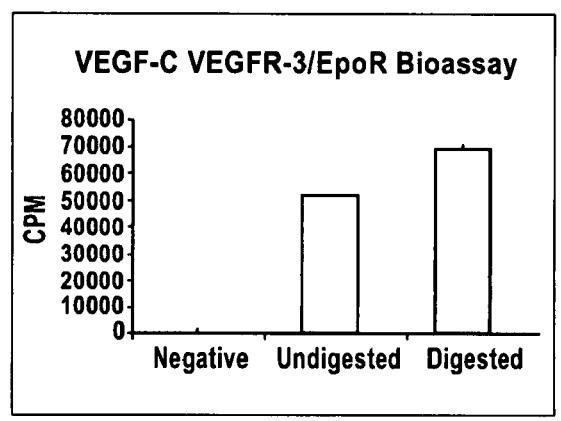

Results are shown in FIG. 5. Plasmin digestion of VEGF-C resulted in a statistically significant increase in proliferation of both the VEGFR-2/Epo and VEGFR-3/EpoR lines. Plasmin, therefore, activates VEGF-C.

Example 8

Blocking of Activation of VEGF-D and/or VEGF-C by Plasmin with Antibodies to VEGF-D and/or Antibodies to VEGF-C Antibodies to full and/or partial length VEGF-D protein were generated by standard methods. Preliminary assays indicated that these antibodies blocked interaction between plasmin and VEGF-D protein. This result will be repeated with antibodies to full and/or partial length VEGF-C.

Example 9

Pharmaceutical Compositions and Diagnostic Kits

Inhibitors of plasmin and/or other activating proteases are combined with appropriate adjuvants to form a pharmaceutically acceptable formulation. "Patient" includes humans and other mammals. "Inhibitors" includes, but is not limited to, monoclonal antibodies, polyclonal antibodies, fragments of said antibodies, and other molecules which inhibit the vascular endothelial growth factor pathway.

Diagnostic kits are also encompassed by the instant invention, including kits encompassing a commercial embodiment of at least one screening assay, which incorporate plasmin or other activating proteases or inhibitors thereof The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

We claim:

1. A method for activating at least one vascular endothelial growth factor selected from the group consisting of purified VEGF-C and purified VEGF-D, comprising treating said at least one vascular endothelial growth factor with a serine protease.

2. The method according to claim 1, wherein the serine protease is plasmin.

3. The method according to claim 2, wherein the plasmin is purified.

4. The method according to claim 1, wherein said at least one vascular endothelial growth factor is in an unprocessed form or a partially processed form.

5. The method according to claim 1, wherein said vascular endothelial growth factor is VEGF-D.

6. The method according to claim 1, wherein said vascular endothelial growth factor is VEGF-C.

7. A method for activating at least one vascular endothelial growth factor selected from the group consisting of VEGF-C and VEGF-D, comprising treating said at least one vascular endothelial growth factor with a purified serine protease.

8. The method according to claim 7, wherein said at least one vascular endothelial growth factor is in an unprocessed form or a partially processed form.

9. The method according to claim 7, wherein said vascular endothelial growth factor is VEGF-D.

10. The method according to claim 7, wherein said vascular endothelial growth factor is VEGF-C.

11. The method according to claim 7, wherein the serine protease is plasmin.

* * * * *